United States Patent [19]

Danho et al.

[11] Patent Number: 4,808,701

[45] Date of Patent: Feb. 28, 1989

[54] CYCLIC PEPTIDES HAVING APPETITE REGULATING ACTIVITY

[75] Inventors: Waleed Danho, Wayne; Joseph Triscari, Bloomfield; Vincent S. Madison, Mountain Lakes, all of N.J.

[73] Assignee: Hoffmann-La Roche Inc., Nutley, N.J.

[21] Appl. No.: 31,632

[22] Filed: Mar. 30, 1987

[51] Int. Cl.$^4$ ............................ C07K 7/50; C07K 7/64
[52] U.S. Cl. ...................................... 530/317; 530/321; 530/329
[58] Field of Search ................................ 530/317, 321

[56] References Cited

U.S. PATENT DOCUMENTS 3,705,140 12/1972 Bernardi et al. ................... 530/329
3,839,315 10/1974 Ondetti et al. ..................... 530/329
4,351,829  9/1982 Zetler et al. ....................... 530/329

OTHER PUBLICATIONS

Durieux et al., Peptide, Structure and Function, Proceedings of the 9th American Peptide Symposium, Editor, Pierce Chemical Company, pp. 575–578 (1985).

*Primary Examiner*—Howard E. Schain
*Assistant Examiner*—Christina Chan
*Attorney, Agent, or Firm*—Jon S. Saxe; George M. Gould; Julie M. Prlina

[57] ABSTRACT

Cyclic peptides with appetite regulating activity.

16 Claims, No Drawings

CYCLIC PEPTIDES HAVING APPETITE REGULATING ACTIVITY

BACKGROUND OF THE INVENTION

There are approximately 34 million Americans at least 20 percent above their desirable weights for whom treatment is advisable, according to the conclusions reached by a recent NIH concensus conference. (National Institutes of Health consensus Panel Report, Feb. 13, 1985; See also *Science,* 1985, 207: 1019–1020.)

In these individuals obesity is a contributory factor to the increased incidence of cardiovascular disease, hypertension, hypercholesterolemia, non-insulin dependent diabetes (NIDD) and cancers of the uterus, breast, gallbladder, colon, rectum and prostate. In addition obesity has a negative weight related impact on mortality; such that in extreme or morbid obesity the mortality ratio may be 1200 percent above normal.

Weight reduction is often recommended as the first course of action for patients suffering from NIDD, hypertension, hypercholesterolemia, coronary artery heart disease, gout and osteoarthritis. However, there are relatively few therapeutic tools which the physician can use to accomplish weight loss. Pharmaceutical agents which are currently used as adjuncts to dietary counseling are effective for short term therapy, but are unacceptable for long term use because of the development of tolerance, their CNS activity and undesirable side effects. Thus, approximately 95% of those patients who successfully lose weight, return to their initial body weights within 12 to 84 months.

An agent which reduces food intake by mimicking the body's own peripheral satiety signals would be expected to be more successful for use in chronic therapy, have fewer adverse side effects and be free of CNS activity.

Cholecystokinin (CCK) is a polypeptide hormone which was first isolated as a 33-amino acid peptide from the porcine gastrointestinal tract. (Mutt et al, *Biochem J.,* 1971, 125: 57–58. Mutt et al., *Clin Endocrinol,* supplement, 1976, 5: 175–183.) Peripherally administered CCK has been shown to produce satiety in the rat, sheep and the monkey (Jorpes et al, *Acta. Chem. Sianel,* 1964, 18: 2408; Della-Fera et al., *Science,* 1979, 206: 471–73; Gibbs et. al, 1973, J. Comp. Physiology and Psychology, 84, 488–495). Infusions of CCK-8, the octapeptide analog of CCK, have been shown to decrease food intake in lean and obese men. (J. Smith, *Int. J. of Obesity,* Vol. 8, Suppl. 1 p. 35–38). It is now accepted that CCK has satiety-inducing effects and thus, may be useful to reduce or suppress food intake in man.

The polypeptide hormone, CCK-33, has the amino acid sequence:

```
     1              5                    10
Lys—Ala—Pro—Ser—Gly—Arg—Val—Ser—Met—Ile—
              15                   20
—Lys—Asn—Leu—Gln—Ser—Leu—Asp—Pro—Ser—His—
                    25
—Arg—Ile—Ser—Asp—Arg—Asp—Tyr(SO3H)—Met—Gly—
                       30      33
                      —Trp—Met—Asp—Phe—NH2.
```

Fragments of CCK, e.g. CCK-8 and CCK-7 also have been shown to have satiety-inducing effects. CCK-8 has the amino acid sequence:

```
 26     27           28    29    30    31    32    33
Asp—Tyr(SO3H)—Met—Gly—Trp—Met—Asp—Phe—NH2.
```

CCK-7 is one amino acid less than CCK-8, i.e., it is CCK-8 minus the 26-position Asp.

The known peptides are of linear configuration. Generally linear peptides are very flexible molecules and lack a well-defined conformation. Each amino acid in a linear peptide is exposed to the surrounding milieu resulting in a peptide much more susceptible to enzymatic and chemical degradation.

Although the linear forms of CCK-33, CCK-8 and its various analogs, as well as CCK-7 are known to have satiety inducing effects, these peptides are short acting. Further, linear CCK-8 for example, degrades very rapidly upon exposure to human gastric juice. Effective oral administration of satiety inducing compounds is thereby precluded. Finding longer acting forms of these satiety inducing compounds as well as an effective route of oral administration is naturally of interest.

SUMMARY OF THE INVENTION

A cyclic peptide is a peptide wherein the beta or gamma carboxy terminus of one amino acid in the peptide chain is attached to the alpha, delta, or epsilon amino terminus of another amino acid in the peptide chain via the formation of an amide bond. The bonding between the two peptides in the chain yields a ring structure.

The biological properties of cyclic peptides are altered considerably relative to those of their linear analogs. Cyclic peptides are much more rigid, with well-defined shapes and interior amino acid residues which are shielded from the surrounding milieu. These changes are reflected in the biological properties of the peptide. The cyclic peptide's duration of action will be longer since the compact structure renders it less susceptible to chemical and enzymatic degradation. The bioavailability of the cyclic peptide will be increased due to changes in the tissue distribution caused by the shielded interior amino acid residues. Further, the well defined shape of the cyclic peptide will give it greater specificity for the target receptor thus reducing the probability of undesirable biological activities concomitant with the desired one. In contrast, with linear peptides there are generally both central and peripheral receptors for a given linear peptide, and there is considerable cross reactivity of a given peptide with receptors for another peptide.

The instant invention is directed to linear peptides of the specific sequence set forth herein. The invention is also directed to the cyclic forms of these peptides. The invention is also directed to linear and cyclic forms of the peptides of the invention or their pharmaceutically acceptable salts. The invention is also directed to methods for suppressing food intake in animals comprising administering to said animal an effective food intake suppressing amount of the peptides of the invention or their pharmaceutically acceptable salts.

In the context of the instant invention, a cyclic peptide is defined as a peptide wherein the beta or gamma carboxy terminus of one amino acid in the peptide chain is attached to the alpha, delta, or epsilon amino terminus of another amino acid in the peptide chain. In the peptides of the instant invention, the following configurations apply unless otherwise stated.

| Amino Acid in chain | Terminus of Amino Acid bound to make cyclic peptide |
|---|---|
| Lys | e amino (e = epsilon) |
| Orn | W amino (W = delta) |
| Tyr(SO$_3$H)) | a amino (a = alpha) |
| Asp | b carboxy (b = beta) |
| Glu | q carboxy (q = gamma) |

The specific cyclic peptides of the instant invention are made by protecting the functional group of the amino acids in the chain where cyclic binding is not desired, leaving the amino acids to be bound together to form the cyclic structure unprotected. In solid phase synthesis methods, the reactive side chain groups of the various amino acid moieties are typically protected with suitable protecting groups which will prevent a chemical reaction from occurring at that site until the protecting groups are ultimatley removed. Each amino acid in the chain can be protected by any protective group conventionally used for the respective amino acid in solution phase synthesis. The unprotected amino acids in the chain will then bind to form the cyclic peptides of the invention, forming a ring structure.

ABBREVIATIONS USED

The following abbreviations or symbols are used to represent amino acids, active groups, projecting groups and the like.

| Symbol | Meaning |
|---|---|
| Ac | Acetyl |
| Orn | Ornithine |
| 2-chloro-Z | 2-Chloro-benzyloxycarbonyl |
| 2 | Benzyloxycarbonyl |
| For | Formyl |
| DMF | Dimethylformamide |
| Boc | tert.-Butyloxycarbonyl |
| TFA | Trifluoroacetic acid |
| CH$_3$CN | Acetonitrile |
| Phe—NH$_2$ | 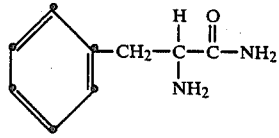 |
| N—methyl-Phe—NH$_2$ | 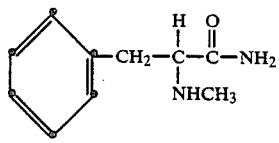 |
| Phe—NHCH$_3$ | 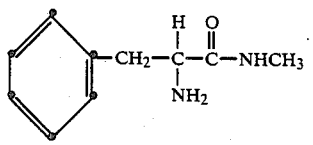 |

| Symbol | Meaning |
|---|---|
| N—methyl-Phe—NHCH$_3$ | 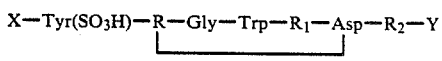 |

Amino acids are given their commonly understood three-letter designation herein, unless otherwise specified, the L-isomer is meant.

DETAILED DESCRIPTION

The invention is directed to cyclic peptides of the formula:

I.

X—Tyr(SO$_3$H)—R—Gly—Trp—R$_1$—Asp—R$_2$—Y wherein

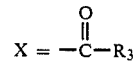

R = Lys, Orn
R$_1$ = Met, Nle
R$_2$ = Phe, N methyl Phe
R$_3$ = lower alkyl
Y = NH$_2$, NHCH$_3$ Particularly preferred are peptides of the formulas:

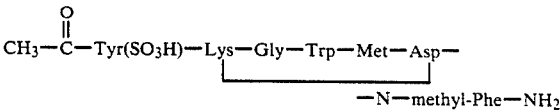

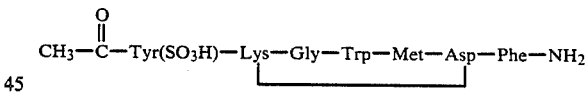

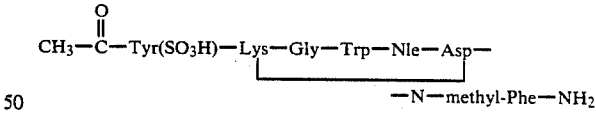

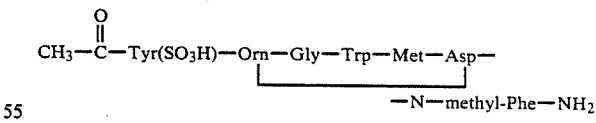

The invention is also directed to peptides of the formula:

II.

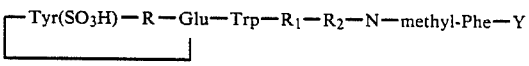

wherein
R = Met, Nle
R$_1$ = Met, Nle
R$_2$ = Thr(SO$_3$H), Ser(SO$_3$H), Hyp(SO$_3$H)

Y=NH$_2$, NHCH$_3$

Particularly preferred is a peptide of the formula

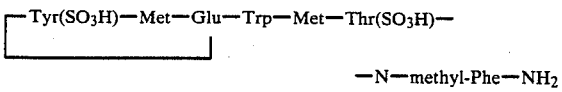

—N—methyl-Phe—NH$_2$

The invention is also directed to peptides of the formula:

III.

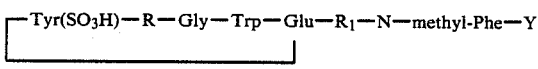

wherein
R=Met, Nle
R$_1$=Thr(SO$_3$H), Ser(SO$_3$H), Hyp(SO$_3$H)
Y=NH$_2$, NHCH$_3$ Particularly preferred is a peptide according to the formula:

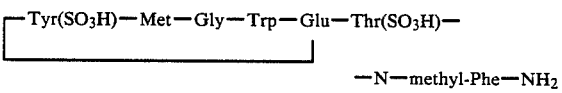

—N—methyl-Phe—NH$_2$

With respect to the peptides of formula I, where R=Lys then it is the ε (epsilon) amino terminus of Lys which is bound to the β (beta) carboxy terminus of Asp to make the cyclic peptide. In formula I where R=Orn, it is the Δ (delta) amino terminus of Orn, which is bound to the β (beta) carboxy terminus of Asp to make the cyclic peptide.

With respect to formula II, it is the α (alpha) amino terminus of Tyr(SO$_3$H) which is bound to the λ (gamma) carboxy terminus of Glu to make the cyclic peptide.

With respect to formula III it is the α (alpha) amino terminus of Tyr(SO$_3$H) which is bound to the λ (gamma) carboxy terminus of Glu to make the cyclic peptide.

The invention is also directed to linear peptides of the formula:

IV.

X-Tyr(SO$_3$H)-R-Gly-Trp-R$_1$-Asp-R$_2$-Y
wherein

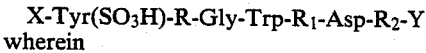

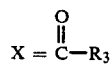

R=Lys, Orn
R$_1$=Met, Nle
R$_2$=Phe, N-methyl-Phe
R$_3$=lower alkyl
Y=NH$_2$, NHCH$_3$

V.

Tyr(SO$_3$H)-R-Glu-Trp-R$_1$-R$_2$-N-methyl-Phe-Y
wherein
R=Met, Nle
R$_1$=Met, Nle
R$_2$=Thr(SO$_3$H), Ser(SO$_3$H), Hyp(SO$_3$H)
Y=NH$_2$, NHCH$_3$

VI.

Tyr(SO$_3$H)-R-Gly-Trp-Glu-R$_1$-N-methyl-Phe-Y
wherein
R=Met, Nle
R$_1$=Thr(SO$_3$H), Ser(SO$_3$H), Hyp(SO$_3$H)
Y=NH$_2$, NHCH$_3$ The peptides of this invention have a satiety inducing effect in animals and are useful to suppress food intake. They may be used in a program to control or reduce the body weight of the animal.

The invention is directed to cyclic peptides of the amino acid sequences set forth in formulas I, II, III or their pharmaceutically acceptable salts, and compositions containing these peptides.

The invention is also directed to linear peptides of the amino acid sequences set forth in formulas IV, V and VI or their pharmaceutically acceptable salts.

The invention is also directed to a method for suppressing food intake in animals comprising administering to said animal effective food intake suppressing amounts of the peptides of the invention.

As used herein the term "food intake suppressing amount" refers to the amount of peptide (on a weight basis) per Kg of body weight of the animal which must be administered to suppress food intake. It is within the skill of the art to calculate such amounts considering the method of administration, the particular animal and the weight of the animal. The level of skill in the art relating to the use of CCK-8 as a satiety agent is illustrated by the references summarized in Morley, J. E., "Minireview The Ascent of Cholecystokinin (CCK) From Gut to Brain" *Life Sciences,* 1982, 479 at 485–488, 30:

PREPARATION OF PEPTIDES OF INVENTION

The process of synthesizing the peptides of the invention is comprised of:

(a) preparing a corresponding blocked linear peptide attached to a solid phase resin.

(b) removing the linear peptide from the resin, and purification by HPLC.

(c) treating the linear peptide with a cyclizing agent to obtain the cyclic peptide through the formation of an amide bond and purification by HPLC.

(d) Sulfation of the cyclic peptide, and purification by HPLC.

(a) Preparing a corresponding blocked linear peptide attached to a solid phase resin The peptides may be prepared using solid phase synthesis by the method generally described by Merrifield, J. Am. Chem. Soc., 85: 21499 (1963) although other equivalent chemical synthesis known in the art may also be used. Solid-phase synthesis is commenced from the carboxy terminus of the peptide by coupling a protected a-amino acid by an amide bond to a suitable resin, e.g., benzylhydrylamine (BHA) or methylbenzylhydrylamine resin (MBHA). BHA and MBHA resin supports are commercially available and generally used when the desired peptide being synthesized has an unsubstituted amide at the carboxy terminus.

All solvents used in the preparations described herein, e.g. methylene chloride (CH$_2$Cl$_2$), 2-propanol, and dimethylformamide (DMF) were Burdick & Jackson "Distilled in Glass" grade and used without additional distillation. Trifluoroacetic acid (TFA), diisopropylethylamine (DIPEA), and dicyclohexylcarbodiimide (DCC) were purchased from Chemical Cyanamid Corporation and were "sequential" grade purity. Ethandithiol (EDT) was purchased from Sigma Chemical Co. and used without further purification. All protected amino acids were of the L configuration unless otherwise indicated and were obtained from Bachem.

In solid phase synthesis methods, the reactive side chain groups of the various amino acid moieties are typically protected with suitable protecting groups which will prevent a chemical reaction from occurring at that site until the protecting group is ultimately removed. While specific protecting groups are disclosed in regard to the solid phase synthesis aspect, it should be noted that each amino acid can be protected by any protective group conventionally used for the respective amino acid in solution phase synthesis. Among such protecting groups there are included for example conventional protecting groups for carboxyl groups selected from esters such as aryl esters, particularly phenyl or phenyl substituted with lower alkyl, halo, nitro, thio or lower alkyl (1–7 carbon atoms) thio. All α-amino groups were blocked with t-butyloxycarbonyl (Boc) functions. Side chain groups were substituted as follows: Asp, Glu, Thr with benzyl; Trp with formyl and Tyr with 2,6-dichlorobenzyl; Lys with 2-chloro-Z, or with Z. Purity of these compounds was confirmed by thin layer chromatography (TLC) and optical rotation. The benzylhydrylamine (BHA) resin was a copolymer of styrene—1% divinylbenzene in bead form (200–400 mesh) obtained from Beckman Instruments. Total nitrogen content was 0.654 meq/g.

The following instrumentation was utilized. Thin layer chromatography (TLC) was performed on glass backed precoated silica gel 60 F254 plates (Merck) using appropriate solvent systems. Detection of spots was by UV fluorescence quenching (254 nm absorption), iodine staining, or ninhydrin spray (for primary and secondary amines).

For amino acid analyses, peptides were hydrolyzed in 6N HCl containing phenol at 115° C. for 24 hours in evacuated Reacti-Therm hydrolysis tubes. Analyses were performed on a Beckman 121M amino acid analyzer.

High performance liquid chromatography (HPLC) was conducted on an LDC apparatus consisting of a Constametric I pump, a Constametric III pump, a Gradient Master solvent programmer and mixer, and a Spectromonitor III variable wavelength UV detector. Analytical HPLC chromatography was performed with Waters Micro Bondapack $C_{18}$ reversed phase columns (0.4×25 cm). Preparative HPLC separations were run on a Whatman (2.5×50 cm) Partisil M20 10/50 ODS-3 column, or (2.3×30 cm) micro Bondapack $C_{18}$ column; in both cases, a pre-column of Whatman Co:Pell ODS pellicular packing was used.

The peptides were assembled in a stepwise manner on a solid support using a Vega 250 peptide synthesizer. The chemistry module was controlled by a Model 300 Microprocessor from Vega Biochemicals with manual operations at step 16 and 20.

Boc-N-methyl-Phe was coupled to the benzylhydrylamine resin (5 g) using Boc-N methyl Phe (5 g, 17 mmol) and DCC (1.8 g, 9 mmol) at 0° C., loading was determined by amino acid analysis to be 0.20 mmol/g resin. Any unreacted amino groups were capped by treating with 6 equivalents each of acetic anhydride and pyridine.

The initial synthesis was started with resin and the protocol for a typical synthetic cycle was as follows:

| Step | Reagent | Time |
| --- | --- | --- |
| 1 | 1% EDT/$CH_2Cl_2$ | 1 × 30 sec |
| 2 | 50% TFA/$CH_2Cl_2$ w/1% EDT | 1 × 1 min |
| 3 | Repeat Step 1 | |
| 4 | 50% TFA/$CH_2Cl_2$ w/1% EDT | 1 × 15 min |
| 5 | $CH_2Cl_2$ | 1 × 30 sec |
| 6 | 2-Propanol | 1 × 30 sec |
| 7–8 | Repeat steps 5 & 6 | |
| 9 | $CH_2Cl_2$ | 2 × 30 sec |
| 10 | 8% DIPEA | 2 × 2 min |
| 11–15 | Repeat step 5–9 | |
| 16 | 5 equiv. Boc-AA anhydride | 1 × 30 min |
| 17 | 1% DIPEA | 1 × 5 min |
| 18–19 | Repeat steps 6 & 9 | |
| 20–21 | Repeat steps 16 & 17 if Kaiser test is positive | |
| 22 | 2-Propanol | 1 × 30 sec |
| 23–24 | Repeat steps 5 & 6 | |
| 25 | $CH_2Cl_2$ | 1 × 30 sec |
| 26 | DMF | 2 × 30 sec |
| 27 | $CH_2Cl_2$ | 3 × 30 sec |

Solvents for all washings and couplings were measured to volumes of 10–20 ml/g resin. Couplings were performed as the symmetrical anhydrides of the Boc-amino acids. They were performed in $CH_2CL_2$ at 0° C. in 15 min. using 10 equivalents of Boc-amino acid and 5 equivalents of DCC.

Coupling reactions were monitored by the Kaiser ninhydrin test to determine whether coupling was complete after step 19. Kaiser, E. et al., *Anal. Biochem.*, 34, 595–598 (1970). Total cycle times ranged from 54–160 minutes per residue.

(b) Removing the linear peptide from the resin and purifications by preparative HPLC The fully assembled peptide-resins were dried under High vacuum overnight. Deblocking and cleavage conditions were the modified procedures of Tam et al. Tetrahedron Letters, 23, 4425, 4438 (1982) and were optimized for CCK-8 analogs generally. The peptide-resin was treated in a teflon HF apparatus (Peninsula) with HF, dimethylsulfide and p-cresol (5:13:2) ml for 1 h at 0° C., after evaporation to a low volume fresh anhydrous HF was distilled into the reaction vessel (18 ml) for a second treatment for 1.5 h at 0° C. After thorough evaporation, the dry resin was washed with 3 volumes each of $Et_2O$ and EtOAc, then titrated with 4×15 ml of 30% acetic acid and filtered. Lyophilization of the aqueous filtrate yielded the crude linear peptide.

Preparative purification were carried out directly on the crude peptide by HPLC on a (2.3×30 cm) micro Bondapack $C_{18}$ or (2.5×50 cm) Whatman ODS-3 column. The peptides were applied in a minimum volume of 50% AcOH, and eluted with a slow gradient (4 hr) of 5–65%, 0.022% TFA/$CH_3CN$, at a flow rate of 8.0 ml/min. Fractions were collected at 3 minute intervals and cuts were made after inspection by analytical HPLC. Fractions, judged to be greater then 97% pure, were pooled and lyophilized.

Purity of the peptide was checked by HPLC and determined to be 99% in all cases. Amino acid analyses of the individual peptides were performed and the expected values were obtained in each case. U.V., I.R., and M.S. were also performed on the analogs confirming the chemical integrity of the peptides.

(c) Treatment of the linear peptide with a cyclizing agent to obtain the cyclic peptide through the formation of an amide bond and purification by HPLC The linear peptide was dissolved in DMF and treated with 3N HCl/Dioxane to protonate the free amino group as the hydrochloride salt. This was treated with diphenylphosphenylazide and activated for 1 hour at −20° C. Then the reaction mixture was diluted (15 volumes) with DMF and N-methyl morpholine was added to a pH of 7.5. The cyclization reaction was carried out for 2 days at +5° C. during which the pH was checked and maintained at neutral (pH 7.4) by the addition of N-methyl morpholine. The "pH" in organic solvent is determined by the application of an aliquot of the solution to moistened narrow range pH paper.

The progress of the cyclization was followed by analyzing an aliquot of the reaction mixture using HPLC. Usually after 1-2 days the starting linear peptide is converted either to the cyclic monomer or to the polymeric forms of the linear peptide.

The crude cyclic peptides obtained were purified by preparative HPLC on a (2.3×30 cm) micro Bondapack $C_{18}$ column. The peptides were applied in a minimum volume of acetic acid and eluted with a slow gradient (4h) of 5–65% 0.022% TFA/$CH_3CN$ at a flow rate of 8.0 ml/min. Fractions were collected at 3 minute intervals and cuts were made after inspection by analytical HPLC. The purity of the cylic peptides was checked by anaytical HPLC, amino acid analysis and M.S.

(d) Sulfation of the cyclic peptide and purification by HPLC

The sulfate-ester containing peptides were prepared by double sulfation of the phenolic (tyrosine) and hydroxy (serine, threonine, or hydroxyproline) groups using pyridine acetyl sulfuric acid reagent. A typical sulfation was carried out as follows: 60–240 mg of pyridinium acetyl sulfate (PAS) was dissolved in 5 ml of pyridine and mixed at 60° C. for 10 minutes. N-acetyl-CCK-8 analog (10 mg) is dissolved in 5 ml of pyridine to which the PAS reagent is added. After heating and mixing for 45–60 min. at 60° C., it is neutralized with 2 volumes 0.05M ammonium bicarbonate, lyophilized and purified by HPLC.

The sulfated peptides were purified by preparative reverse phase HPLC on a $C_{18}$-10 m (ES Industries) (1.25×30 cm) column using a 2 hour gradient (10–40%) of acetonitrile in 0.05M ammonium bicarbonate with a flow rate of 5 ml/min and detection of 240 nm. Fractions to be pooled and peptide purity were determined by analytical HPLC using a Bondapack $C_{18}$, 10 m Waters column (0.30×30 cm), and an acetonitrile in ammonium bicarbonate gradient with a flow of 2 ml and detection at 215 nm.

The purity of the sulfated peptides was determined by analytical HPLC, amino acid analysis, UV, IR, MS and NMR.

The following examples illustrate in detail the preparation of the appetite regulating activity peptides of the invention utilizing the procedure described above. In the examples described below, unless otherwise stated, the peptides were characterized and their purity was determined using amino acid analysis, analytical HPLC, UV, IR and MS.

EXAMPLE 1

Preparation of

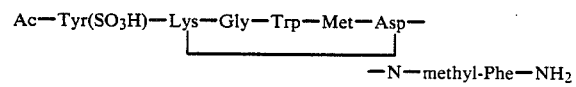

Boc-N-methyl-Phe (5 g, 17.8 mmol) was dissolved in a mixture of 50 ml methylene chloride and 50 ml of dimethylformamide chilled to 0° C. and with stirring (1.8 g, 9 mmol) dicyclohexylcarbodiimide was added and the mixture was stirred for 60 minutes at 0° C.

Separately 5 g of benzylhydrylamine copolysterene 1% divinylbenzene cross-linked resin (0.56 mmole N/g) was washed with 10% diisopropylethylamine in methylene chloride for 30 min, filtered and washed with methylene chloride, dimethylformamide, and methylene chloride. The chilled mixture above was added to the resin and stirred for 24 hours at room temperature. The resin was filtered, washed with methylene chloride, dimethylformamide, isopropanol, methylene chloride, dimethylformamide, isopropanol, and methylene chloride, and dried under high vacuum.

Amino acid analysis showed the resin to contain 0.20 mmoles of N-methylphenylalanine per gram of resin. Unreacted amino groups were capped by shaking the resin with 5 ml of acetic anhydride and 5 ml diisopropylethylamine in methylene chloride for 60 minutes. The resin was filtered and washed with methylene chloride, isopropanol, dimethylformamide and methylene chloride. 4.8 g (0.96 mmole) of Boc-N-methylphenylalanine resin was subjected to sequential solid phase synthesis using the procedure described above. All couplings were performed using the symmetrical anhydrides of Boc-amino acids as described. At step 16 and 20 the activated amino acids were added with the corresponding reaction times as follows: six individual cycles were performed with Boc-aspartic acid-b-benzyl ester (1.6 g, 5 mmole, 60 min., 1.6 g, 5 mmole, 60 min.), Boc-methionine (1.25 g, 5 mmole, 30 min., 1.25 g, 30 min. 5 mmole), Boc-$N^{in}$-formyl-tryptophan (1.70 g, 5 mmole, 30 min., 1.70 g, 5 mmole, 30 min.), Boc-glycine (900 mg, 5 mmole, 30 min., 900 mg, 5 mmole, 30 min.), Boc-e-2-chloro-Z-Lysine (2.10 g, 5 mmol, 30 min., 2.10 g, 5 mmole, 30 min.) and Boc-2-6-dichlorobenzyl-tyrosine (2.2 g, 5 mmole, 30 min., 2.2 g, 5 mmole, 30 min.).

Deprotection of the Boc-protecting group and acetylation of the resin with 20 ml acetic anhydride, 20 ml of pyridine in methylene chloride for 60 min. yielded 5.2 g of the acetylated-heptapeptidyl resin.

1.9 g of the resin was cleaved by treatment with 25 ml of HF containing dimethylsulfide (2 ml) anisole (1 ml) and dithioethane (0.7 ml) for 1 hour at 20° C. After thorough evaporation the resin was washed with 2 volumes of ethylacetate, then titrated with 4×15 mL of 30% acetic acid filtered and lyophilized to yield 300 mg of crude peptide.

150 mg of the crude peptide was purified by preparative HPLC on a (2.3×30 cm) micro Bondapack $C_{18}$ column. The peptide was eluted with a linear gradient of 5 to 65%, 0.022% TFA/$CH_3CN$ at a flow rate of 8 ml/min., detection was at 280 nm. The main peak was collected and lyophilized to yield 20 mg (11%) Ac-Tyr-Lys-Gly-Trp-Met-Asp-N-methyl-Phe-$NH_2$. This material was homogenous by HPLC and gave the correct amino acid analysis and MS. As is (19 mg, 0.02 mmol) of the linear peptide was dissolved in 1 ml of DMF and 0.1 ml of 3M HCl/Dioxane was added. The reaction mixture was evaporated to dryness and redissolved in 1 ml of DMF. Diphenylphosphorylazide (0.13 ml, 0.005 mmol) was added after the mixture had been cooled to $-20°$ C. and the mixture was allowed to stir for 1 hour at $-20°$ C. After this the reaction mixture was diluted with 15 ml of DMF, and the pH was adjusted to 7.5 (as measured by moistened pH sticks) with N-methylmorphine. The reaction mixture was warmed to 5° C. and allowed to stand for 2 days at this temperature at pH 7.4. The pH was maintained with addition of small aliquots of N-methylmorphine.

The reaction mixture was concentrated in vacuo and the residue was dissolved in 1 ml of acetic acid and applied to a (2.3×30 cm) micro Bondapack $C_{18}$ column. The column was eluted with a slow gradient (4 h) of 5–65%, 0.022% TFA/CH$_3$CN at a flow rate of 8.0 ml/min. Detection was at 280 nm. Fractions were collected at 3 minute intervals and cuts were made after inspection by anaytical HPLC. The peak corresponding to the cyclic peptide was collected and lyophilized to yield 8 mg (45%) of the:

This material was homogenous by HPLC and gave the following amino acid analysis: Asp 1.00 (1); Gly 1.07 (1); Met 1.00 (1); Tyr 1.12 (1); Lys 1.00 (1); Trp and N-methyl-phe were not determined, and have the correct MS.

Emp. Form. $C_{49}H_{62}N_{10}O_{10}S$ MW 982.14.

To 190 mg of pyridine acetyl sulfate (PAS) was added 10 ml of dry distilled pyridine. The resulting mixture was heated at 60° C. with stirring for 10 min. The solution was allowed to cool, and 8.0 mg of

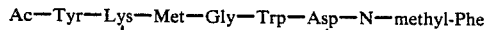

dissolved in 10 ml of pyridine was added to the solution and the reaction mixture was stirred for 1 hour at 60° C. Thereafer, the reaction mixture was neutralized with 2 volumes of ammonium bicarbonate and lyophilized.

Purification was achieved by preparative reverse phrase HPLC on an ES Industries $C_{18}$-10 column (1.25×30 cm) using a linear gradient of 10–40% of 0.05M NH$_4$HCO$_3$/CH$_3$CN in 120 min. with a flow rate of 5 ml/min and detection at 240 min. the yield was 7.0 mg (87%) of

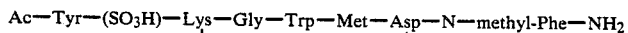

Amino Acid analysis: Asp 1.00(1); Gly 1.00(1); Met 1.00(1); Tyr 1.12(1); Lys 1.00(1); Trp and N-methyl Phe n.d.

Emp. form. $C_{49}H_{62}N_{10}O_{13}S_2$ MW 1063.21.

EXAMPLE 2

Preparation of

4.0 g (0.8 mmol) of Boc-N-methylphenylalanine resin which was obtained in the same way as in Example 1 was subjected to sequential solid phase synthesis using the same procedure as in Example 1. All couplings were performed using the symmetrical anydrides of Boc-amino acids as described before. At step 16 and 20 the activated amino acids were added with the corresponding reaction times as follows: six individual cycles were performed with Boc-O-benzyl-threonine (1.5 g, 5 mmole, 60 min, 1.5 g, 5 mmol, 60 min), Boc-methionine (1.25 g, 5 mmole, 30 min, 1.25 g, 5 mmole, 30 min), Boc-N$^{in}$-formyltryptophan (1.7 g, 5 mmole, 30 min. 1.7 g, 5 mmol, 30 min). Boc-glutamic acid-λ-benzylester (1.6 g, 5 mmole, 30 min.) 1.6 g, 5 mmole, 30 min.), Boc-methionine (1.25 g, 5 mmole, 30 min., 1.25 g, 5 mmole, 30 min.) and Boc-2,6-dichlorobenzyl-tyrosine (2.2 g, 5 mmole, 30 min. 2.2 g, 5 mmole, 30 min). Deprotection of the Boc-protecting group is carried out as described in example 1 to yield 4.9 g at the heptapeptidyl resin.

1 g of the resin was cleaved by treatment with 5 ml of HF containing dimethylsulfide (12 ml). p-cresol (2.0 ml) and dithioethane (1 ml) for 1 hour at 0° C. After evaporation to a low volume, fresh anhydrous HF (18 ml) was distilled into the reaction vessel for a second treatment for 2 h at 0° C. After thorough evaporation, the resin was washed with ethylacetate, then titrated with 30% acetic acid and filtered, lyophilized to yield 210 mg of crude peptide. 100 mg of this crude peptide was purified by preparative HPLC on a (2.3×30 cm) micro Bondapack $C_{18}$ column. The peptide was eluted with a linear gradient of 5–65%, 0.022% TFA/CH$_3$CN at a flow rate of 8 ml/min., detection was at 280 nm. The main peak was collected and lyophilized to yield 15 mg (19%) of NH$_2$-Trp-Met-Glu-Trp-Met-Thr-N-methyl-Phe-NH$_2$ this material was homogenous by HPLC and gave the correct amino acid analysis and MS.

15 mg (0.02 mmol) of the linear peptide was cyclized using diphenylphosphorylazide as described in detail in example 1 to yield 6 mg (41% yield) of

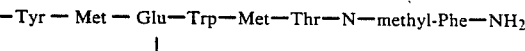

this material was homogenous by HPLC and gave the following amino acid analysis: Thr 0.90(1) Glu 1.00; (1) Met 2.00(2); Tyr. 1.00(1); Trp 0.80(1); N-methyl-Phe N.D. and have the correct MS. Emp. form. $C_{49}H_{63}N_9O_{10}S_2$ MW 1002.0.

To 80 mg of pyridine acetyl sulfate (PAS) was added 6 ml of dry distilled pyridine. The resulting mixture was heated at 60° C. with stirring for 10 min. The solution was allowed to cool and 3 mg of

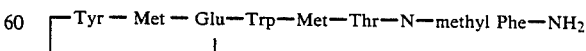

dissolved in 3 ml of pyridine was added to the solution and the reaction mixture was stirred for 1 hour at 60° C.

Thereafter, the reaction mixture was neutralized with 2 volumes of ammonium bicarbonate, and lyophilized. Purification was achieved by preparative reverse phase HPLC on an ES-Industries C$_{18}$-10 micron column (1.25×30 cm) using a linear gradient of 10–40% of 0.05 NH$_4$HCO$_3$/CH$_3$CN in 120 min. with a flow rate of 5 ml/min and detection at 240 min. the yield was 1.4 mg (45%) of Tyr(SO$_3$H)-Met-Glu-Trp-Met-Thr(SO$_3$H)-N methyl Phe-NH$_2$ Amino acid analysis: Thr 0.85(1); Glu 1.00(1); Met. 1.80(2); Tyr. 1.00(1); Trp. 0.75(1); N-methyl-Phe n.d. mp. form. C$_{49}$H$_{63}$N$_9$O$_{18}$S$_4$ MW. 1162.32.

EXAMPLE 3

Preparation of

⌐Tyr(SO$_3$H) — Met — Gly — Trp — Glu—Thr(SO$_3$H)—N methyl Phe—NH$_2$
└─────────────────────────────────────────────┘

5.0 g (1 mmol) of Boc-N-methylphenylalanine resin which was obtained in the same way as in Example 1 was subjected to sequential solid phase synthesis using the same procedure as in Example 1. All couplings were performed using the symmetrical anhydrides of Boc-amino acids as described before. At step 16 and 20 the activated amino acids were added with the corresponding reactions times of follows: six individual cycles were performed with Boc-O-benzyl-threonine (1.5, 5 mmole, 60 min. 1.5 g, 5 mmole, 60 min.): Boc-glutamic acid-q-benzylester (1.6 g, 5 mmole, 30 min., 1.6 g, 5 mmole, 30 min.); Boc-N$^{in}$-formyl-tryptophan (1.7 g, 5 mmole, 30 min., 1.7 g, 5 mmole, 30 min); Boc-glycine (900 mg, 5 mmole, 30 min., 900 mg, 5 mmole, 30 min.); Boc-met (1.25 g, 5 mmole, 30 min., 1.25 g, 5 mmole, 30 min.) and Boc-2,6-dichlorobenzyl-tyrosine (2.2 g, 5 mmole, 30 min, 2.2 g, 5 mmole, 30 min).

Deprotection of the Boc-protecting group is carried out as described in example 1 to yield 5.80 g of the heptapeptidyl resin. 2.4 g of the resin was cleaved by treatment with HF containing dimethylsulfide, p-cresol and dithioethane using the same procedure of example 2. The resin was washed with ethylacetate, then titrated with 30% acetic acid, filtered and lyophilized to yield 452 mg of crude peptide.

100 mg of the crude peptide was purified by preparative HPLC on a (2.3×30 cm) micro Bondapack C$_{18}$ column. The peptide was eluted with a linear gradient of 5 to 65% 0.022% TFA/CH$_3$CN at a flow rate of 8 ml/min. Detection was at 280 nm. The main peak was collected and lyophilized to yield 20 mg (23% of NH$_2$-Tyr-Met-Gly-Trp-Glu-Thr-N-methyl-Phe-NH$_2$. This material was homogeneous by HPLC and gave the correct amino acid analysis and MS.

20 mg (0.02 mmol) of the linear peptide was cyclized using diphenylphosphorylazide as described in detailing in example 1 to yield 4 mg (21% yield) of ⌐Tyr — Met — Gly — Trp—Glu—Thr—N—methyl-Phe—NH$_2$
└─────────────────────────────────────────────┘

This material was homogenous by HPLC and gave the following amino acid analysis: Thr 0.90(1); Glu 1.00(1); Gly 1.00(1); Met 0.90(1); Tyr 0.97(1); Trp 0.63(1); N-methyl-Phe n.d. and have the correct MS. Emp. formula C$_{46}$H$_{57}$N$_9$O$_{10}$S M.W. 928.07.

4 mg. of

⌐Tyr — Met — Gly — Trp—Glu—Thr—N—methyl-Phe—NH$_2$
└─────────────────────────────────────────────┘ was dissolved in 5 ml of pyridine and added to a solution of 80 mg of pyridinum acetyl sulfate (PAS) in 5 ml of pyridine, prepared in the same manner as described in Example 1. The reaction mixture was stirred for 1 h at 60%, then neutralized with 2 volumes of ammonium bicarbonate, and lyophilized.

Purification was achieve by preparative HPLC using the same condition as described in Example 1. The yield was 3.8 mg. (94%) of ⌐Tyr — (SO$_3$H) — Met — Gly — Trp—Glu—Thr(SO$_3$H)—N—methyl-Phe—NH$_2$
└──────────────────────────────────────────────────────┘

Amino acid analysis: Thr 0.90(1); Glu 1.04(1); Gly 1.01(1); Met 0.85(1); N-methyl-Phe-and Trp n.d.
Emp. formula C$_{46}$H$_{57}$N$_9$O$_{16}$S$_3$ M.W. 1088.20.

EXAMPLE 4

In Vitro Receptor Binding Assay

Frozen bovine striatum (approx. 5 g) and fresh rat pancreas (approx. 5 g) cleaned of fat and extraneous tissue were homogenized in HEPES buffer #1 (10 mM HEPES+130 mM NaCl+5 mM MgCl$_2$, pH 7.4) using 35 parts buffer per 1 part tissue on a wet weight/volume basis (approx. 175 ml). The tissue was homogenized 2× for approx. 15 sec. at 0° C. using a Polytron homogenizer at a setting of 6. The tissue was isolated by centrifugation at 48,000×g for 10 min. at 0° C. The resulting tissue pellet was resuspended in HEPES buffer #2 (10 mM HEPES+130 mM NaCl+5 mM MgCl$_2$+1 mg/L phenylmethanesulfonyl fluoride (PMSF)+200 mg/L Bacitracin): 1 part striatal tissue (original wet weight) per 80 parts buffer and 1 part pancreas tissue (original wet weight) per 70 parts buffer.

Incubation was initiated by combining various concentrations of native CCK-8 or peptides of formula 1 with $^3$H-CCK-8-(SO$_3$H) (final conc.=0.15 nM) and tissue homogenate (striatum 0.26 mg protein in 2 ml final volume; pancreas 0.165 mg protein in 1 ml final volume). Samples were incubated for 30 min. at 25° C. and the incubation terminated by pouring the mixture onto a pre-wet Whatman GF/B filter on a Sandbeck Vacuum Filtration Manifold. The incubation tubes were washed with 2×3 ml of ice-cold HEPES Buffer #2 and the wash filtered through the GF/B filter. The filter was air dried for 10 min. and then placed in a scintillation vial with 12 ml of Beckman HP/b Ready-Solv scintillation cocktail. The vials were shaken for 2-12 hours and then counted using a Beckman Model 7800 liquid scintillation spectrometer. Non-specific binding was determined in the presence of 1 uM native CCK-8 and subtracted from all samples to determine specific binding. The concentration of peptide necessary to inhibit 50% of total specific $^3$H-CCK-8-(SO$_3$H) binding (IC$_{50}$ value) was determined by log-probit analysis.

The results are summarized in Table 1.

have food ad libitum over the entire 24-hour day. On the fourth day, the rats were weighed again, and any which lost more than five grams body weight were excluded from the test. The animals were then distributed into experimental (n=5 to 6) and control groups (n=6-12), but not matched for body weight.

Peptides of the invention were suspended either in saline, if soluble, or in 1% gum arabic, if insoluble, at concentrations of 32 to 320 μg/ml/kg body weight and were administered intraperitonerally 15 min before the first meal on day 5 of meal feeding. The rats were then

TABLE 1

| Peptide Sequence | Example No. | Bovine Striatum nM | Rat Pancreas nM | Dose microgm/kg | Food Intake 1st Meal % of Control | Food Intake 2nd Meal % of Control |
|---|---|---|---|---|---|---|
| H—Asp—Tyr(SO$_3$H)—Met—Gly—Trp—Met—Asp—Phe—NH$_2$ | CCK-8 | 1-4.6 | 1-3.2 | 32 | 27 ± 17 | 149 ± 6* |
| Ac—Tyr(SO$_3$H)—Lys—Gly—Trp—Met—Asp—N methyl Phe—NH$_2$ | 1 | 3000 | 1500 | 32<br>320 | 72 ± 10<br>14 ± 5*** | 133 ± 6*<br>145 ± 10** |
| Ac—Tyr(SO$_3$H)—Lys—Gly—Trp—Met—Asp—Phe—NH$_2$ |  | >1000 | 45 | 32<br>320 | 81 ± 6*<br>43 ± 7*** | 111 ± 4 N.S.<br>135 ± 5*** |
| Ac—Tyr(SO$_3$H)—Lys—Gly—Trp—Nle—Asp—N methyl Phe—NH$_2$ |  | >1000 | 6600 | 320 | 77 ± 10* | 132 ± 10** |
| Ac—Tyr(SO$_3$H)—Orn—Gly—Trp—Met—Asp—N methyl Phe—NH$_2$ |  | 52000 | 13000 | 320 | 72 ± 10* | 141 ± 9* |
| Tyr(SO$_3$H)—Met—Glu—Trp—Met—Thr(SO$_3$H)—N methyl Phe—NH$_2$ | 2 | >1000 | 5400 | 320 | 52 ± 7*** | 131 ± 9** |
| Tyr—(SO$_3$H)—Met—Gly—Trp—Glu—Thr(SO$_3$H)—N methyl Phe—NH$_2$ | 3 | >10000 | >10000 | 320 | 73 ± 10* | 114 ± 13 N.S. |

Values significantly different than their respective controls
***p ≦ 0.001,
**p ≦ 0.01,
*p ≦ 0.05
Ns = not significant

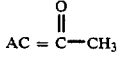

AC = C—CH$_3$

EXAMPLE 5

Two-Meal Feeding Assay

Male Sprague-Dawley (CD) rats weighing 180-200 grams (Charles River Breeding Laboratories) were acclimated to a 12 h light/dark cycle (6 a.m. to 6 p.m.) in a room kept at 22° C. They were subsequently fasted for two days, weighed, placed in individual cages, and a four-day period of meal training was begun. During this time the rats were given ground laboratory chow (Purina Lab Chow) in jars for one hour from 9:00 a.m. until 10:00 a.m., the jars were removed from 10:00 a.m. to 12:00 p.m., and placed back in the cages from 12:00 until 1:00 p.m. Under this '1-2-1' meal feeding regime, most rats learn to eat approximately as much per day during the two hours they have access to food as rats which given their meals as they had been during the previous four days, and the food cups were weighed both before and after each meal to determine food consumption. Food intake was expressed as a mean and standard error of the mean as a percent of control values for the various groups. The treated groups were compared to the control groups by t-test analysis. The results are summarized in Table 1.

EXAMPLE 6

Gastric juice (400 microliters) and (200 micrograms) of peptide of Example 1

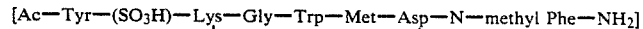

and CCK-8 [H-Asp-Tyr-(SO$_3$H)-Met-Gly-Trp-Met-Asp-Phe-NH$_2$] were incubated at 37° C. for varying periods of time. The degradation was monitored by analytical HPLC on a micro Bondapack ($C_{18}$ column (0.4×30 cm) with a linear gradient of 10–40% of 0.01M $NH_4Ac/CH_3CN$ in 40 min. with a flow rate of 2 ml/min and detection at 225 nm.

Rates are based on presumed production of the unsulfated

for Example 1 and the disappearance of the peak corresponding to the CCK-8 for example CCK-8.

| Peptide | Time of Incubation in (min) | % Degradation by area |
|---|---|---|
| Example 1 | 0 | 0 |
|  | 60 | 1.4 |
|  | 180 | 3.6 |
|  | 1380 | 12.8 |
| CCK-8 | 0 | 0 |
|  | 15 | 90 |
|  | 60 | 100 |

We claim:

1. A peptide of the formula

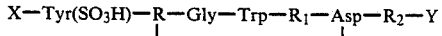

wherein

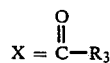

R=Lys, Orn
$R_1$=Met, Nle
$R_2$=Phe, N-methyl-Phe
$R_3$=lower alkyl
Y=$NH_2$, $NHCH_3$ or the pharmaceutically acceptable salts thereof.

2. The peptide of claim 1 wherein

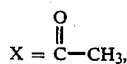

R=Lys, Orn; $R_1$=Met, Nle; $R_2$=N-methyl-Phe or Phe; and Y=$NH_2$.

3. The peptide of claim 2 wherein R=Lys; $R_1$=Met, Nle; $R_2$=Phe, N-methyl-Phe.

4. The peptide of claim 3 wherein $R_1$=Met; and $R_2$=N methyl-Phe having the formula

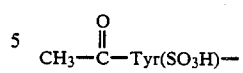
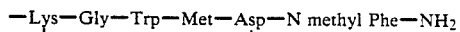

5. The peptide of claim 3 wherein $R_1$=Met; $R_2$=Phe having the formula

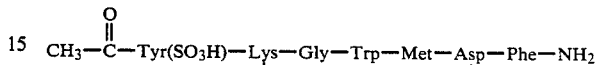

6. The peptide of claim 3 wherein $R_1$=Nle; $R_2$=N-methyl-Phe having the formula

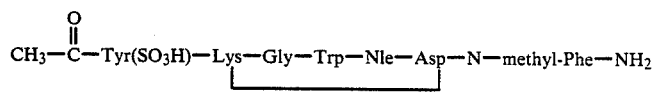

7. The peptide of claim 2 where R=Orn and $R_1$=Met $R_2$=N-methyl-Phe having the formula

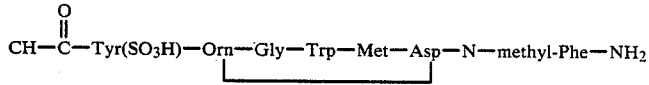

8. A peptide of the formula

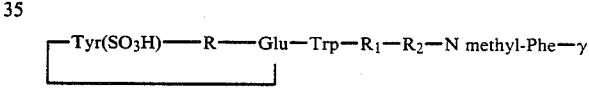

wherein
R=Met, Nle
$R_1$=Met, Nle
$R_2$=Thr($SO_3H$), Ser($SO_3H$), Hyp($SO_3H$)
Y=$NH_2$, $NHCH_3$ or the pharmaceutically acceptable salts thereof.

9. The peptide of claim 8 wherein R=Met, Nle; $R_1$=Met, Nle; $R_2$=Thr($SO_3H$), Ser($SO_3H$), Hyp($SO_3H$); and Y=$NH_2$.

10. The peptide of claim 9 wherein R=Met, $R_1$=Met, Nle; $R_2$=Thr($SO_3H$), Ser($SO_3H$), Hyp($SO_3H$).

11. The peptide of claim 10 wherein $R_1$=Met and $R_2$=Thr($SO_3H$) having the formula

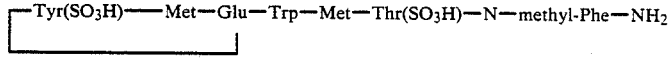

12. A peptide of the formula

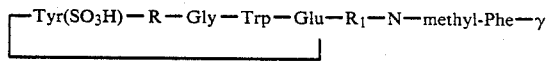

wherein
R=Met, Nle
$R_1$=Thr($SO_3H$), Ser($SO_3H$), Hyp($SO_3H$)
Y=$NH_2$, $NHCH_3$ or the pharmaceutically acceptable salts.

13. The peptide of claim 12 wherein R=Met, Nle; $R_1$=Thr(SO$_3$H), Ser(SO$_3$H), Hyp(SO$_3$H) and Y=NH$_2$.

14. The peptide of claim 13 wherein R=Met; $R_1$=Thr(SO$_3$H), Ser(SO$_3$H), Hyp(SO$_3$H).

15. The peptide of claim 14 wherein $R_1$=Thr(SO$_3$H) having the formula

⌐Tyr(SO$_3$H)—Met—Gly—Trp—Glu—Thr(SO$_3$H)—N—methyl-Phe—NH$_2$
└─────────────────┘

16. A peptide selected from the group consisting of:

X—Tyr(SO$_3$H)—R—Gly—Trp—R$_1$—Asp—R$_2$—Y    (a)
         └──────────────┘ wherein

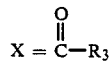

R=Lys, Orn
$R_1$=Met, Nle
$R_2$=Phe, N-methyl-Phe $R_3$=lower alkyl
Y=NH$_2$, NHCH$_3$ ⌐Tyr(SO$_3$H)—R—Glu—Trp—R$_1$—R$_2$—N—methyl-Phe—Y    (b)
└────────────────────┘ wherein
R=Met, Nle
$R_1$=Met, Nle
$R_2$=Thr(SO$_3$H), Ser(SO$_3$H), Hyp(SO$_3$H)
Y=NH$_2$, NHCH$_3$ ⌐Tyr(SO$_3$H)—R—Gly—Trp—Glu—R$_1$—N—methyl-Phe—Y    (c)
└────────────────────┘ wherein
R=Met, Nle
$R_1$=Thr(SO$_3$H), Ser(SO$_3$H), Hyp(SO$_3$H)
Y=NH$_2$, NHCH$_3$
or the pharmaceutically acceptable salts.

* * * * *